United States Patent [19]
Sand

[11] Patent Number: 6,113,602
[45] Date of Patent: Sep. 5, 2000

[54] POSTERIOR SPINAL INSTRUMENT GUIDE AND METHOD

[75] Inventor: Paul M. Sand, Roseville, Minn.

[73] Assignee: Sulzer Spine-Tech Inc., Minneapolis, Minn.

[21] Appl. No.: 09/276,982

[22] Filed: Mar. 26, 1999

[51] Int. Cl.$^7$ ...................................................... A61L 17/56
[52] U.S. Cl. ............................... 606/61; 606/99; 623/17
[58] Field of Search ................................. 606/61, 90, 99, 606/96; 623/17; D24/135; 600/567; 604/264

[56] References Cited

U.S. PATENT DOCUMENTS

| | | |
|---|---|---|
| D. 397,436 | 8/1998 | Michelson . |
| 4,501,269 | 2/1985 | Bagby . |
| 5,015,247 | 5/1991 | Michelson . |
| 5,055,104 | 10/1991 | Ray . |
| 5,250,055 | 10/1993 | Moore et al. ............................ 606/96 |
| 5,458,638 | 10/1995 | Kuslich et al. . |
| 5,484,437 | 1/1996 | Michelson . |
| 5,489,307 | 2/1996 | Kuslich et al. . |
| 5,489,308 | 2/1996 | Kuslich et al. . |
| 5,505,732 | 4/1996 | Michelson . |
| 5,609,636 | 3/1997 | Kohrs et al. . |
| 5,658,337 | 8/1997 | Kohrs et al. . |
| 5,741,253 | 4/1998 | Michelson . |
| 5,797,909 | 8/1998 | Michelson . |
| 5,865,857 | 2/1999 | Kohrs et al. . |

FOREIGN PATENT DOCUMENTS

| | | |
|---|---|---|
| 0 796 593 A2 | 9/1997 | European Pat. Off. . |
| WO 98/17208 | 4/1998 | WIPO . |

OTHER PUBLICATIONS

"Ray Cervical Threaded Fusion Cage," *Surgical Dynamics*, 1994.

*Primary Examiner*—Michael Buiz
*Assistant Examiner*—Julian W. Woo
*Attorney, Agent, or Firm*—Merchant & Gould P.C.

[57] ABSTRACT

The present invention provides instruments and methods for insertion of spinal implants into the intervertebral space between opposing vertebral bodies. Instrumentation according to the invention includes an instrument guide having a first member and a second member each having a tubular proximal region and a distal region having a lateral guide surface. The instruments and methods of the invention are particularly advantageous for placement of spinal implants using a posterior approach to the vertebrae.

20 Claims, 6 Drawing Sheets

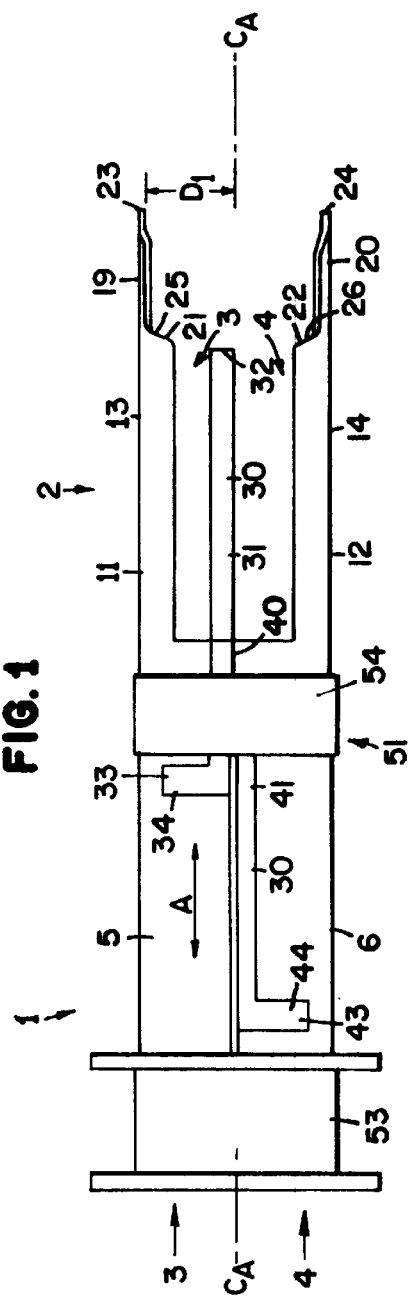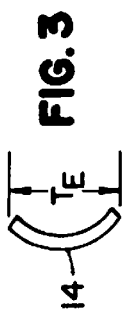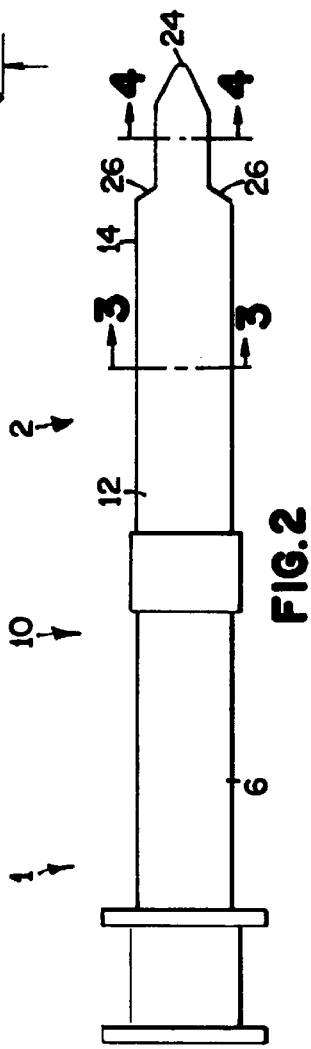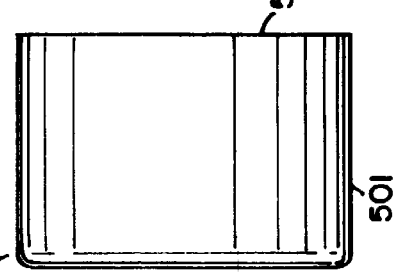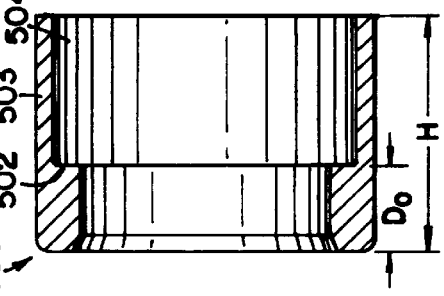

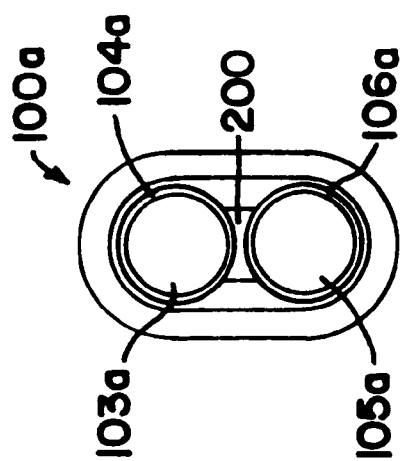
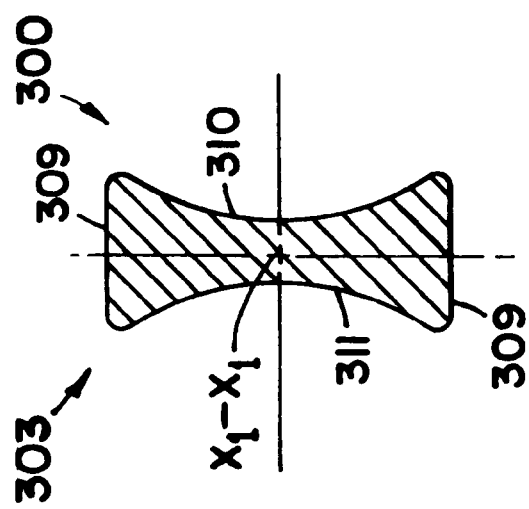

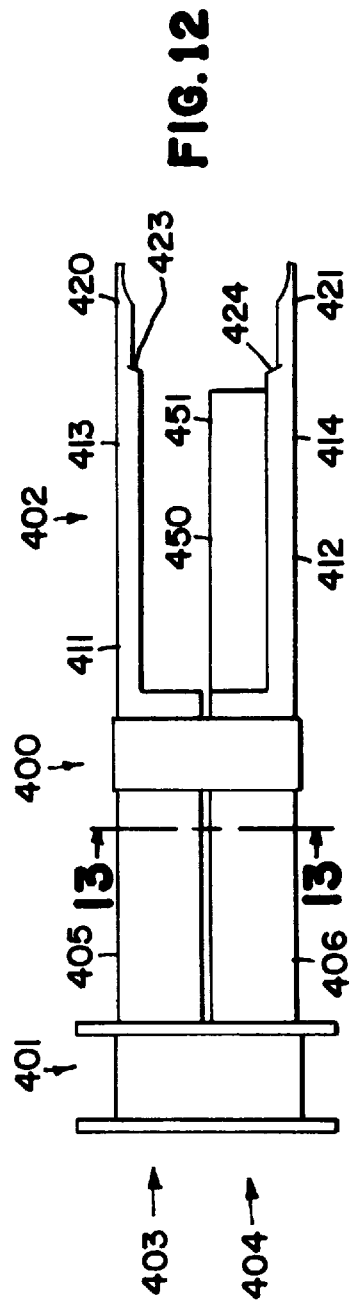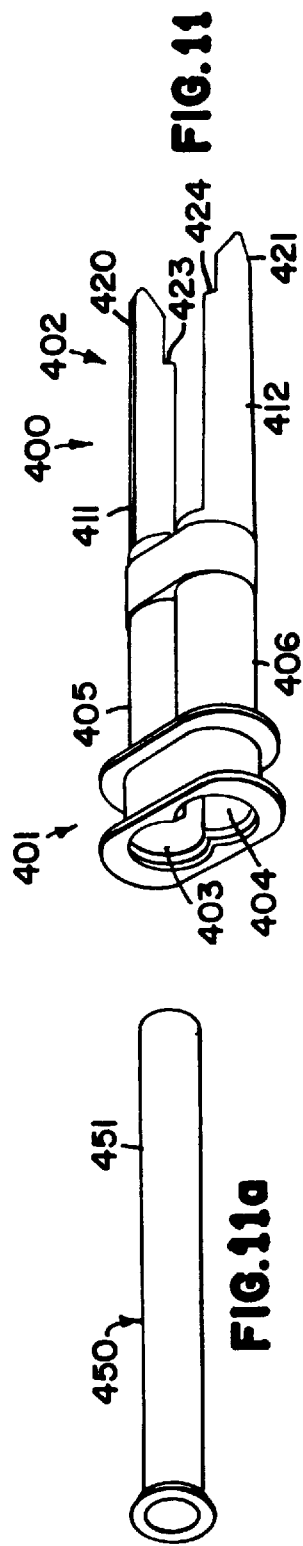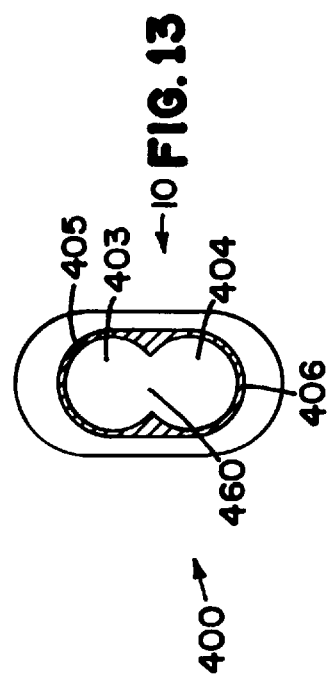

POSTERIOR SPINAL INSTRUMENT GUIDE AND METHOD

FIELD OF THE INVENTION

This invention pertains to intervertebral fusion. Specifically, the invention is directed to instrumentation and methods for insertion of spinal implants between opposing vertebral bodies through a posterior approach.

BACKGROUND OF THE INVENTION

Chronic back problems can cause pain and disability for a large segment of the population. Frequently, the cause of back pain is traceable to diseased disc material between opposing vertebrae. When the disc material is diseased, the opposing vertebrae may be inadequately supported, resulting in persistent pain.

Surgical techniques have been developed to remove the diseased disc material and fuse the joint between opposing vertebral bodies. Arthrodesis of the intervertebral joint can reduce the pain associated with movement of an intervertebral joint having diseased disc material. Generally, fusion techniques involve removal of the diseased disc, distraction, drilling a bore for receiving the implant and inserting the implant between the opposing vertebral bodies.

Spinal fusion implants and related surgical instruments for implanting a fusion device are known and disclosed in, for example, U.S. Pat. Nos. 5,741,253; 5,658,337; 5,609,636; 5,505,732; 5,489,308; 5,489,307; 5,484,437; 5,458,638; 5,055,104; 5,026,373; 5,015,247; 4,961,740 and 4,501,269. The disclosure of each of these patents are incorporated herein by reference. Procedures for fusing an intervertebral joint space typically include placement of at least two cylindrical implants in parallel arrangement between the opposing vertebrae.

Some presently available systems for intervertebral fusion provide for preparing an implant site through a hollow tube. Procedures for preparing an implant site through a hollow tube are shown in, for example, U.S. Pat. Nos. 5,484,437; 5,489,307 and 5,505,732. The disclosure of each of these patents are incorporated herein by reference. In some procedures, the implants are also inserted into the prepared site through the hollow tube. Preparing the implant site by passing instruments through a hollow tube advantageously provides for an isolated surgical field with reduced chance of injury to soft tissues surrounding the surgical site.

However, generally, several steps are required for appropriate placement of the implants using present hollow tube systems. These steps include inserting a spacer into the disc space to distract one side of the intervertebral space, then inserting a second spacer for distracting the second side of the vertebral space, followed by placement of the hollow tube over or through a guiding mechanism to orient the longitudinal axis of the implant site relative to the vertebral column. Once the hollow tube is secured in proper alignment, reamers, bores, taps, or other instruments are passed through the hollow tube to prepare the implant site. Either before or after the implant is inserted into the first site, the hollow tube is removed and the procedure is repeated on the opposite side.

Present procedures for placement of an implant through a hollow tube help to reduce the chance of iatrogenic tissue trauma caused by the implant procedure. However, while known procedures provide for reduced chance of injury, the surgeon's accuracy in the relative placement of the hollow tube between the first and second sides is still a matter of guess work and repeated verification using fluoroscopy or radiographic monitoring is needed. Also, the need for individual placement of the hollow guide tube using such methods (i.e., one placement for each implant site) increases the possibility for relative misalignment of the implants to occur during insertion.

One system for decreasing the likelihood of relative misalignment of adjacent implants has been through the use instrument guides comprising dual lumens in fixed relationship to one another. Examples of such instruments are disclosed in U.S. Pat. Nos. 5,055,104; 5,484,437 and 5,797,909. Additional multi-lumen instrument guide systems are disclosed in co-pending U.S. Ser. Nos. 09/081,240 and 09/116,747 which are assigned to Sulzer Spine-Tech Inc., the assignee of the present invention. The disclosure of each of these patents and patent applications are incorporated herein by reference.

However due to the anatomical location of the spinal cord traversing the posterior aspect of the vertebral bodies, presently available dual-lumen guide systems are unsuitable for spinal implant procedures performed from the posterior aspect of the patient's body.

Thus, there is a need for the precision, safety and ease of placement of spinal fusion implants provided by a dual-lumen guide system when the procedure is performed from the posterior aspect of the patient. The present invention is directed to addressing this need.

SUMMARY OF THE INVENTION

The present invention provides enhanced precision for placement of spinal fusion implants between opposing vertebral bodies, particularly from a posterior approach. Spinal implant procedures using the instrumentation and methods of the invention also reduce the number of steps necessary for performing a spinal implant procedure.

Throughout the specification, guidance may be provided through lists of examples. In each instance, the recited list serves only as a representative group. It is not meant, however, that the list is exclusive.

The invention provides instruments and methods for insertion of spinal implants into the vertebral space between opposing vertebral bodies. While the instruments and methods may be used for either an anterior or posterior approach, they are particularly advantageous for a posterior approach. The instruments include an instrument guide having a first member including a first proximal region having a tubular configuration and a first distal region having a first lateral guide surface. Fixed adjacent and parallel to the first member is a second member including a second proximal region having a tubular configuration and a second distal region having a second lateral guide surface. Each of the first and second lateral guide surfaces can have a distal extension or paddle extending distally therefrom. The paddle may or may not have a tapered distal tip.

The disclosed instrument guides also have a medial guide surface in the distal region which can be selectively removed or retracted for guiding instruments passed through the lumen.

The invention also provides methods for using the instrument guides of the invention.

DETAILED DESCRIPTION OF THE DRAWINGS

FIG. 1 is a top plan view of an instrument guide according to the present invention;

FIG. 2 is a side view of the instrument guide of FIG. 1, the opposite side view being identical;

FIG. 3 is a transverse cross-section view taken through line 3—3 of FIG. 2;

FIG. 4 is a transverse cross-section view taken through line 4—4 of FIG. 2;

FIG. 7 is a transverse cross-section view taken through line 7—7 of FIG. 5 of an alternative embodiment of an instrument guide according to the invention;

FIG. 10 is a transverse cross-section through line 10—10 of the centering guide of FIG. 8; and FIG. 11 is a perspective view of an alternative embodiment of an instrument guide according to the invention;

FIG. 11a is a perspective side view of an alternative embodiment of a medial guide surface according to the invention;

FIG. 12 is a top view of the instrument guide of FIG. 11;

FIG. 13 is a cross-section view through line 13—13 of the instrument guide of FIG. 12;

FIG. 14b is a perspective side view of the medial guide surface illustrated in FIG. 14a;

FIG. 15b is a perspective side view of the medial guide surface illustrated in FIG. 15a;

FIG. 16 is a long side plan view of one embodiment of a stopping arrangement according to the invention; and FIG. 17 is a long side cross section view of the embodiment of a stopping arrangement illustrated in FIG. 16.

DETAILED DESCRIPTION OF THE INVENTION

Figure 5:
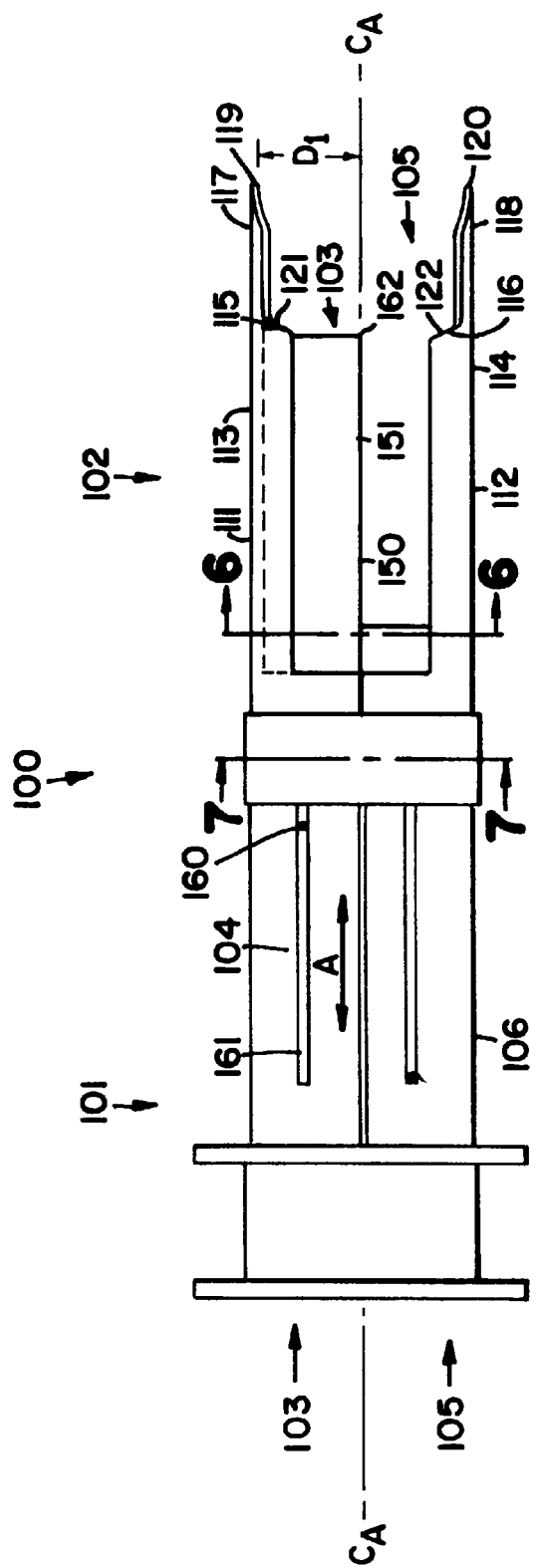
FIG. 5 is a top plan view of an alternative embodiment of an instrument guide according to the present invention.

The instruments and methods of the present invention facilitate the ease and accuracy of placement of multiple spinal implants into a vertebral space between opposing vertebrae. The complementary interaction of the herein disclosed component instruments can also reduce the number of intraoperative images needed to establish the relative alignment of the implants during an implant procedure.

The ability to enhance the accuracy of alignment between two implants inserted into the intervertebral disc space according to the procedures of the invention is facilitated by early establishment and continued maintenance of parallel operating fields at multiple implant sites. Once the surgeon has determined the angular orientation of the implant (e.g., relative to the sagittal and/or transverse plane of the vertebral column), the instrumentation disclosed ensures that the relative positioning of the implants is maintained throughout preparation of the bores that will receive the implants.

Some instruments useful with the new instruments described herein are known and disclosed in, for example, U.S. Pat. Nos. 5,489,307, 5,865,847 and co-pending patent application Ser. Nos. 08/921,001 and 09/116,747, the entire disclosures of which are incorporated herein by reference. These disclosures include various distraction plugs, centering guides, guide pins, reamers, taps, etc., which may be used with the new instruments disclosed herein.

In one embodiment, the present invention is directed to an instrument guide for guiding instruments used to prepare a site for implantation of a spinal fusion implant. While the herein disclosed instrument guides are particularly advantageous for performing fusions through a posterior approach, it will be appreciated that the instrument guides can also be used for anterior procedures.

In general, the disclosed instrument guides include a proximal region and distal region. The proximal region including openings for inserting instruments into the instrument guide and the distal region including components which are placed against the posterior surface of the vertebrae to be fused. The proximal region of the instrument guide can also include affirmative stop arrangements for selectively controlling the depth of distal penetration of an instrument passed through the instrument guide. Such affirmative stop arrangements suitable for use with an instrument guide according to the present invention include drill depth guides such as spacer caps disclosed in, for example, co-pending U.S. Ser. Nos. 09/081,240 and 09/116,747. Screw adjustable insertion guides such as disclosed in U.S. Ser. No. 08/921,001 can also be used. The disclosure of each of the foregoing patent applications are incorporated herein by reference.

The distal end region of the instrument guides include lateral instrument guide surfaces. Generally, the medial guide surfaces are retractable or removable. Thus, providing instrument guides with portions of the distal guide surfaces which can be selectively removed permits placement of the instrument guides against the posterior surface of adjacent vertebrae without injury to the spinal cord.

It will be appreciated that the present invention is applicable for use with a wide variety of implants including threaded implants and non-threaded implants. The term "implant" as used herein includes bone implants (e.g., autograft, allograft, artificial bone) and non-bone implants made from titanium or other implantable material.

DETAILED DESCRIPTION OF THE ILLUSTRATED EMBODIMENT

With reference to the several drawing figures in which identical elements are numbered identically throughout, a description of some embodiments of an instrument guide according to the present invention will now be provided.

FIG. 1 is a top view of one embodiment of an instrument guide 10 according to the invention. Instrument guide 10 provides for accurate relative alignment of parallel implants inserted from a posterior approach. Instrument guide 10 includes a proximal region 1 and a distal region 2. The proximal region 1 includes a first tubular lumen 3 and a second tubular lumen 4. Lumen walls 5 and 6, which surround lumens 3 and 4, respectively, are substantially complete. However, slots or other openings may be provided through the wall to facilitate cleaning or removal of debris from the instrument.

Distal region 2 of instrument guide 10 includes opposing lateral guide surfaces 11 and 12. First lateral guide surface 11 forms a first partial wall 13 around the distal aspect of first lumen 3 which opens at the proximal end 1 of wall 5. Similarly, second lateral guide surface 12 forms a second partial wall 14 around the distal aspect of second lumen 4 which opens at the proximal end 1 of wall 6.

A distal extension or paddles 19 and 20 extend from the distal ends 21 and 22 of the first lateral guide surface 11 and second lateral guide surface 12, respectively. In the illustrated embodiment, a tapered distal tip 23, 24 is present at the distal end of each of paddles 19 and 20. The tapered distal tip 24 of wall 14 is best appreciated in FIG. 2 which is a side view of instrument guide 10. The side view of the opposite side of instrument 10 is identical to that of FIG. 2. The tapered distal tips 23, 24 of paddles 19 and 20 are optional. As will be discussed below, if instrument guide 10 is used with distraction plugs such as described in U.S. Pat. No. 5,489,307 or a central distracter such as described in co-pending U.S. Ser. Nos. 08/921,001 and 09/116,747 tapered distal tips 23 and 24 may not be present. In the event that paddles 19 and 20 are the sole means for distraction of the intervertebral space, tapered distal tips 23 and 24 will facilitate insertion of the paddles between adjacent vertebrae. It will be appreciated that tapering the tips of paddles 19 and 20 can also facilitate placement of the paddles even when another distraction system is used.

FIG. 3 is a transverse cross-section through second partial wall 14 at line 3—3 and FIG. 4 is a transverse cross-section through paddle 20 at line 4—4. As illustrated, the transverse cross-section dimension $T_E$ of second partial wall 14 is greater than the transverse cross-section dimension $T_D$ of distal extension 20. The shoulders 25, 26 formed at the transition between partial walls 13, 14 and paddles 19, 20 provide an affirmative stop to the depth of penetration of paddles 19, 20 when the paddles are inserted into the intervertebral space. In general, the transverse cross-section dimension $T_E$ of partial walls 13 and 14 need only be greater than the transverse cross-section dimension $T_D$ of distal extension 19 and 20, respectively, by an amount sufficient to create a shoulder 25, 26 which can affirmatively stop the depth of penetration of instrument guide 10 into the intervertebral joint space. The length of distal extensions 19, 20 are preferably less than the anterior-posterior dimension of the intervertebral space.

Referring back to FIG. 1, at the distal region, an axial or medial aspect of lumen 3 can be defined by medial guide surface 30. In FIG. 1, the medial guide surface 30 is in the form of a first radiused guide wall 31. First radiused guide wall 31 can be removable from instrument guide 10. As used herein, a "removable" guide surface means that the guide surface can be removed from the distal region 2 by removal from the instrument guide 10 or by retraction to a proximal position 1 or similar displacement which provides for selective presence or absence of a guide surface which opposes the lateral guide surfaces. In the illustrated embodiment, radiused guide wall 31 can selectively slide in the directions of arrow A such that some or all of the axial length of wall 31 lies over the exterior of wall 5 of first tubular lumen 3. When radiused wall 31 is distally advanced, the distal end 32 of radiused wall 31 is in approximate transverse alignment with the distal end 21 of partial wall 13. The proximal end 33 of medial guide surface 30 includes a handle 34 for grasping when sliding the medial guide surface 30 proximally or distally.

To provide a medial guide surface 30 for the distal region of lumen 4, radiused guide wall 31 can be removed from its position opposing first lateral guide surface 11 and reinstalled to oppose second lateral guide surface 12. Preferably, however, a second radiused guide wall 41 forms a second medial guide surface 40 for second tubular lumen 4. As illustrated, the proximal end 43 of radiused guide wall 41 can also include a handle 44 for grasping when sliding guide wall 41 proximally or distally.

At the proximal end 50 of proximal region 1 of instrument 10 and at the distal end 51 of proximal region 1, the walls 5, 6 surrounding lumens 3, 4 are fixed in parallel alignment by collars 53 and 54, respectively. In one embodiment, collar 53 can be configured for mounting a drill depth guide such as a spacer cap as fully described in U.S. Ser. Nos. 09/116, 747 and 09/081,240.

The interior diameter of lumens 3 and 4 that is formed by each lateral guide surface 13, 14 and its opposing medial guide surface 30, 40, in distal region 2, can vary among guide instruments 10. That is, each instrument guide 10 is configured with a particular interior lumen diameter $D_1$ for passing reamers, taps, or implants of a selected diameter in close tolerance with the interior lumen guide surfaces. Suitable interior lumen diameters $D_1$ can correspondence with an implant diameter of 3, 5, 7, 9, 11, 13, 15, 17, 19 or 21 mm as discussed in, for example U.S. Pat. No. 5,489,307. In addition, the transverse dimension $T_D$ of paddles 19 and 20 can be configured to provide a predetermined distraction spacing between adjacent vertebrae.

FIG. 5 is a top view of an alternative embodiment of an instrument guide 100 according to the present invention, having a proximal region 101 and a distal region 102. The proximal region 101 of instrument guide 100 includes a first tubular lumen 103 surrounded by lumen wall 104 and a second tubular lumen 105 surrounded by lumen wall 106. At distal region 102, instrument guide 100 also includes a first lateral guide surface 111 and a second lateral guide surface 112. First lateral guide surface 111 forms a first partial wall 113 around the distal region of first lumen 103 and the second lateral guide surface 112 forms a second partial wall 114 around the distal region of lumen 105. Each lateral guide surface 111, 112 has a distal end 115, 116, respectively. As with instrument guide 10, distal to the distal end 115 and 116 each lateral guide surface 111 and 112 include a distal extension or paddles 117 and 118. A tapered distal end can be present on paddles 117 and 118. Shoulders 121 and 122 are present at the junction of distal ends 115, 116 and paddles 117, 118, respectively, as described above.

In contrast to the instrument guide 10, however, medial guide surface 150 of instrument guide 100 is provided by a hollow sleeve 151. The hollow sleeve of second tubular lumen 106 is not visible as it is retracted within tubular lumen 106. The operation of the hollow sleeves will be described by reference to sleeve 151 and lateral guide surface 111.

Sleeve 151 can move proximally and distally within the interior of lumen 103 in the directions of arrow A. Sleeve 151 is illustrated in the distal extended position. By moving handle 160 in the proximal direction of arrow A, sleeve 151 can be slidably retracted within lumen 103. When sleeve 151 is at full distal extension as illustrated, the distal end 162 of hollow sleeve 151 is in transverse alignment with the distal end 115 of lateral guide surface 111. In the illustrated embodiment, handle 160 travels in track 161. The interior lumen diameter $D_1$ of sleeve 151 is sized for passing instruments through the instrument guide to create the site for the size of the implant to be implanted. The exterior arc of wall 162 of hollow sleeve 151 fits snugly with the interior arc of lateral guide surface 111 to limit substantial lateral movement.

In an alternative embodiment, an instrument guide of the invention can include first and second tubular members wherein the tubular members are separable. Referring to instrument guide 10 of FIGS. 1–6 as an aid for understanding this embodiment, a first tubular member, such as lumen 3 surrounded by corresponding wall 5 and lateral guide surface 11, can be independently positioned at the vertebral surfaces and paddle 19 if present, inserted into the disc space. Once positioned, a second tubular member, such as lumen 4 surrounded by corresponding wall 6 and lateral guide surface 12, can be positioned adjacent and parallel to the first tubular member. The first and second tubular members can then be fixed in parallel alignment using a collar constructed and arranged for coupling the tubular members in a fixed arrangement to provide a desired alignment between the tubular members. Other features of an instrument guide having separable tubular members, including paddles, medial guide surfaces, etc., can be included as disclosed herein for other instrument guides.

Figure 6:
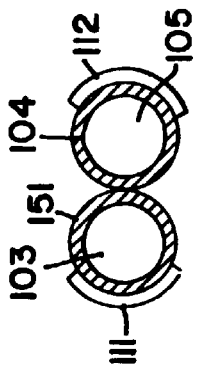
FIG. 6 is a transverse cross-section view taken through line 6—6 of the instrument guide of FIG. 5.
Figure 9:
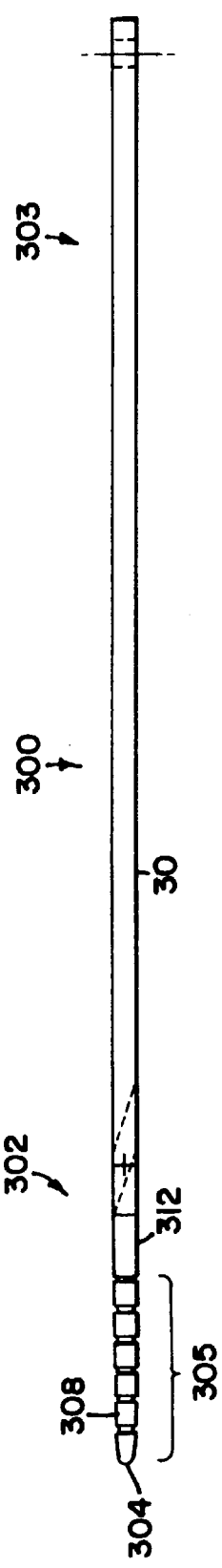
FIG. 9 is a top view of the centering guide of FIG. 8.
Figure 8:
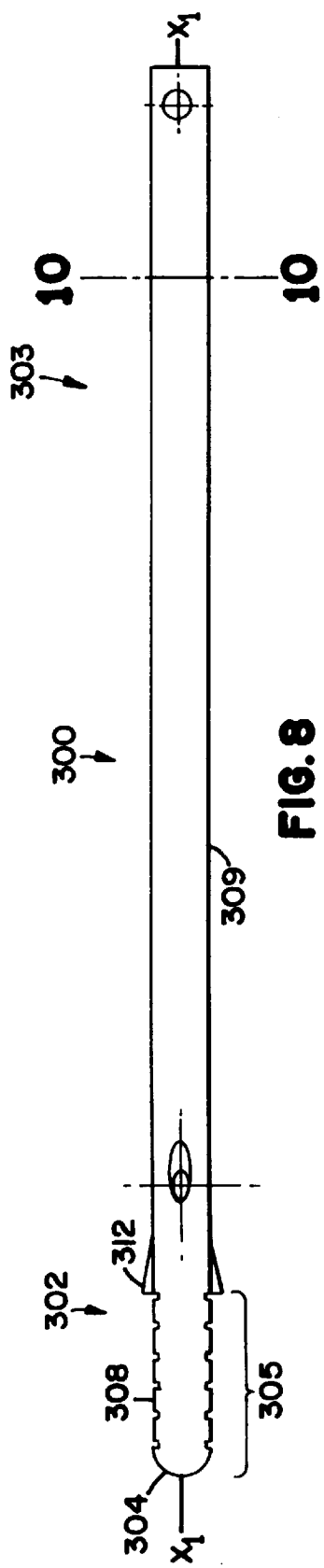
FIG. 8 is a side view of a centering guide.

Another embodiment of an instrument guide 100a will be described by reference to embodiment 100 of FIGS. 5 and 6 and embodiment 100a of FIG. 7. FIG. 6 is a transverse cross-section through line 6—6 of FIG. 5. FIG. 7 is a transverse cross-section through the location of line 7—7 of FIG. 5 of an alternative embodiment of an instrument guide 100a. Comparing FIGS. 6 and 7 it will be appreciated that in the embodiment of FIG. 7, lumen walls 104a, 106a surrounding tubular lumens 103a and 105a, respectively, arranged to form a space 200 between walls 104a and 106a. Space 200 is configured for cooperative fit with the cross-section configuration of the proximal end of a centering guide 300 such as that illustrated in FIGS. 8–10. Centering guides such as that of FIGS. 8–10 are fully described in U.S. Ser. No. 09/116,747, the entire disclosure of which is incorporated herein by reference. By arranging the lumen walls 104a and 106a to permit guided passage of the proximal end 303 (described below) of centering guide 300 into space 200, distraction between adjacent vertebrae may be accomplished through the use of central distraction procedures fully described in U.S. Ser. No. 09/116,747.

In another embodiment, an instrument guide of the invention provides for parallel insertion of spinal implants in close proximity. Examples of implants for close proximity insertion are disclosed in U.S. Pat. Nos. 5,658,337 and 5,609,636, the entire disclosures of which are incorporated herein by reference. Referring to FIG. 11, instrument guide 400 is illustrated in perspective view. Instrument guide 400 includes a proximal region 401 and a distal region 402. A first tubular lumen 403 and a second tubular lumen 404 are surrounded by lumen walls 405 and 406, respectively. At the distal region 402, instrument guide 400 includes first lateral guide surface 411 and second lateral guide surface 412. First lateral guide surface 411 forms a partial wall 413 around the distal aspect of first lumen 403 and the second lateral guide surface 412 forms a second partial wall 414 around the distal aspect of second lumen 404. Distal extensions or paddles 420 and 421 extend from the distal ends 423 and 424 of first lateral guide surface 411 and second lateral guide surface 412, respectively. Medial guide surface 450 is described below.

FIG. 12 is a top view of instrument guide 400 showing medial guide surface 450 in the form of a sleeve 451 which can be passed into either lumen 403 or 404 after instrument guide 400 has been positioned at a location against the exterior surface of the vertebrae. FIG. 11a shows sleeve 451 separated from instrument guide 400. FIG. 13 is a transverse cross-section view through line 13—13 of FIG. 12. As illustrated in FIG. 13, lumen walls 405 and 406 are incomplete at common region 460 where the circular geometry of lumen 403 and 404 overlap one another. The overlapping geometry of the cross-sectional surface area of lumens 403 and 404 provides for reduced spacing between the longitudinal axes of parallel spinal fusion implants when instrument guide 400 is used for preparing the implant sites.

Thus, in use, after instrument guide 400 is positioned against the vertebral bodies, sleeve 451 can be passed into lumen 403 for preparing a first implant site and insertion of a first implant. Sleeve 451 can subsequently be removed and inserted into lumen 404 for preparing a second implant site and insertion of a second implant.

Distraction plugs, obturators, reamers, taps, drill depth guides, and other instrumentation suitable for use with instrument guide 400 are fully disclosed in co-pending U.S. Ser. No. 09/081,240, the entire disclosure of which is incorporated herein by reference.

Figure 14B:
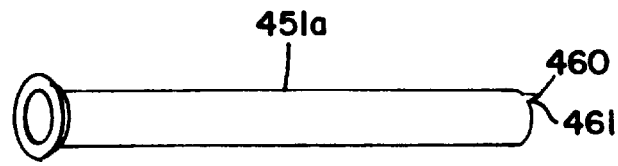
Figure 14A:
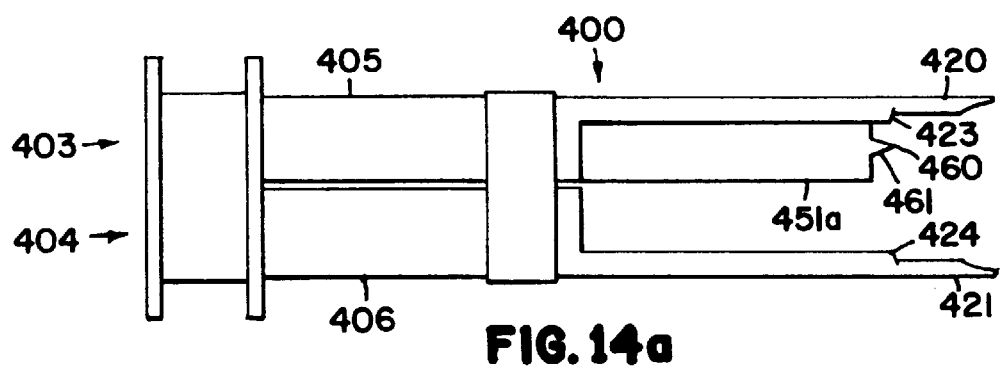
FIG. 14a is a top view of the instrument guide of FIG. 11 including an alternative embodiment of a medial guide surface.
Figure 15B:
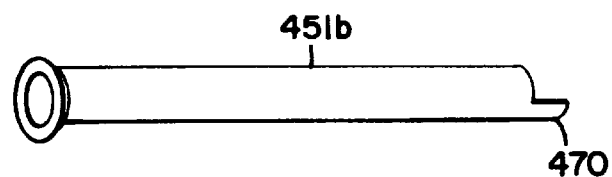

FIGS. 14–15 illustrate alternative sleeve embodiments 451a and 451b. As illustrated in FIGS. 14 and 14a, sleeve 451a can include an anchoring arrangement 460 comprising a tooth 461 which can be embedded into the exterior surface of the vertebrae to facilitate maintenance of the position of instrument guide 400a when at a desired location. Although not illustrated, a second tooth can be positioned diametrically opposed to first tooth 461. Additional teeth can also be used.

Figure 15A:
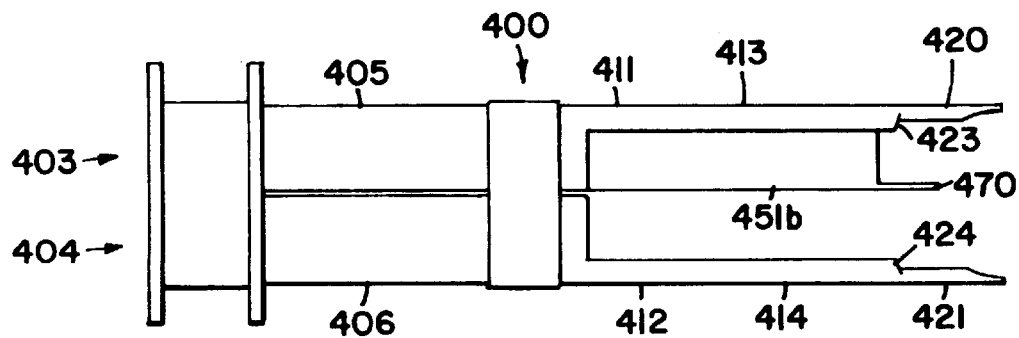
FIG. 15a is a top view of the instrument guide of FIG. 11 illustrating an alternative embodiment of the medial guide surface.

FIGS. 15 and 15a illustrate sleeve 451b including paddle 470. According to this embodiment, in addition to the lateral paddles 420, 421 at the distal end of lateral guide surfaces 411 and 412, paddles 470 can assist distraction as well as facilitate increased maintenance of the position of instrument guide 400b when in a desired location.

Drill Depth Guide

The proximal ends of the disclosed instrument guides can include arrangements for controlling the depth of penetration of instruments passed through the instrument guide. Any suitable arrangement providing an affirmative stop system can be used. Preferred systems include spacer caps and screw type systems as disclosed in U.S. Ser. No. 09/116,747. One embodiment of an arrangement for controlling the depth of penetration of instruments is a stopping arrangement 500 such as spacer cap 501 illustrated in long side plan view in FIG. 16. In FIG. 16, spaver cap 501 is oriented for placement at the proximal end of collar 53 of instrument guide 10 in FIG. 1. A long side cross section of spacer cap 501 is shown in FIG. 17. As illustrated, spacer cap 501 includes a shoulder 502 projecting axially from wall 503 surrounding lumen 504 of spacer cap 501.

Surgical Technique

The instrument guides of the present invention can be used for posterior or anterior approaches to the vertebral column. However, the disclosed instrument guides are particularly advantageous for use when implanting a spinal fusion implant through a posterior approach. Known methods can be used for anesthetizing, positioning and preparing the patient for surgery. Most surgical techniques using the instrument guides of the invention will include a bilateral laminectomy of sufficient size to accommodate the exterior dimensions of the instrument guide.

A. Distraction with Instrument Guide Paddles

In this procedure, the distal extension or paddles of instrument guides 10, 100 of the invention, are used to distract the intervertebral space between adjacent vertebrae. The instrument guide to be used is selected based on a desired lumen diameter and paddle dimension. The interior diameter of the lumen $D_1$ and the transverse dimension of the paddle $T_D$ are selected based on the size of the implant and the amount of distraction needed for the particular intervertebral space. Methods for determining the amount of intervertebral distraction and implant size are within the knowledge of one skilled in the art.

After determining vertebral space to be fused, the central axis $C_A$ of the instrument guide (FIGS. 1 and 5) is aligned with the midsagittal plane of the intervertebral disc space. The tapered distal tips of the paddles are placed against the posterior aspect of the disc with the cauda equina between and safely away from the paddles. Slits can be cut into the disc with a scalpel blade to mark the location of entry for the tapered distal tips of the paddles. The angular orientation of the instrument guide is confirmed and the proximal end of the instrument guide tapped to insert the paddles into the intervertebral space until the depth of insertion is affirmatively stopped by the shoulders at the junction between the paddles and the distal end of the lateral guide surfaces.

Once the instrument guide is positioned, the surgeon selects the side of the intervertebral space to be prepared first and the cauda equina is retracted laterally to the opposite side. After confirming that the cauda equina and nerve roots are sufficiently laterally retracted to prevent injury, the medial guide surface, such as radiused guide wall 31 or sleeves 151, 451, 451*a* or 451*b*, is advanced distally until the distal end of the medial guide surface contacts the posterior aspect of the vertebrae. Once this step is complete, the medial and lateral guide surfaces surrounding the lumen provide guidance for passing reamers, taps and the implant from the proximal region of the instrument guide through the distal region to prepare a site and implant an implant. After implantation of the first side is completed, the cauda equina is retracted laterally over the completed first side and the procedure is repeated on the opposite side of the intervertebral space.

B. Distraction with Distraction Plug

In an alternative embodiment, the instrument guide 10, 100 can be used with the instruments disclosed in U.S. Pat. No. 5,489,307. After the surgeon has selected the appropriate implant size, the dura and cauda equina are retracted laterally over the first side of the intervertebral space to be implanted. At the second side, with the cauda equina and nerve roots clear, the appropriate sized distraction plug is selected and inserted as described in U.S. Pat. No. 5,489, 307. After the distraction plug is inserted on the second side, the cauda equina is retracted laterally over the first side and a distraction plug is placed at the first side of the intervertebral space. Subsequently, a tube guide can be threaded onto the proximal end of the first side distraction plug. The retraction of the cauda equina is released and after confirming the dura and nerve roots are clear, the instrument guide 10, 100 is passed over the drill guide until the paddles are positioned lateral to the lateral aspect of each distraction plug at the posterior aspect of the disc space. Once in the desired position, slits can be cut into the disc with a scalpel blade to mark the location of entry of the paddles into the disc space. The instrument guide can then be tapped lightly until the shoulders at the distal end of the lateral guide surface affirmatively stop distal advancement.

The cauda equina is then retracted over the distraction plug on the second side. The medial guide surface, such as radiused guide wall 31 or sleeves 151, 451, 451*a* or 451*b*, on the first side is advanced distally before or after removal of the distraction plug. The implant site can then be prepared through the instrument guide lumen as described above and in U.S. Pat. No. 5,489,307. After completion of the first side, the medial guide surface is removed or retracted proximally and the cauda equina retracted laterally over the first implant and the procedure is repeated on the opposite side.

It will be appreciated that the instrument guide can be positioned after insertion of one distraction plug and one drill guide, after insertion of two distraction plugs and no drill guide or after insertion of two distraction plugs and one drill guide, etc.

The foregoing method can also be used to insert parallel implants in close proximity using instrument guide 400. Distraction plugs, obturators, drill depth guides and other instruments suitable for insertion of implants in close proximity are disclosed in U.S. Ser. No. 09/081,240, the entire disclosure of which has previously been incorporated by reference.

C. Distraction with a Centering Guide

In an alternative method, an instrument guide according to the present invention can be used with a centering guide as illustrated in FIGS. 7–10 and fully described in U.S. Ser. No. 08/921,001.

Centering guide 300, is a rigid rod extending from a distal end 302 to a proximal end 303 along a longitudinal axis $X_1$—$X_1$. The distal end 302 is rounded at the distal tip 304 to facilitate easy insertion of the distal end 302 into the disc space. In the illustrated embodiment, the distraction portion 305 of the distal end 302 is defined by parallel and spaced-apart side edges 308 which are spaced apart by a distance equal to the desired distraction of the vertebrae. The side edges 308 act against the end plates of the opposing vertebrae to urge the vertebrae apart. The end plates hold the centering guide 300 with the $X_1$—$X_1$ axis centrally positioned between the end plates. While the proximal end 303 can be moved left or right relative to the vertebrae, the precise central positioning of the proximal end 303 can be determined through x-ray analysis following placement of the centering guide 300 such that a surgeon can be assured that the longitudinal axis $X_1$—$X_1$ extends perpendicular to a transverse plane of the vertebrae.

As best illustrated in FIG. 10, which is a cross-section through 10—10 of FIG. 8, extending between side edges 309 of the proximal end 303 and extending the length from end 302 to end 303, are left and right (or first and second) lateral surfaces 310 and 311. The lateral surfaces 310 and 311 are concave and have a radius of curvature equal to a radius of curvature of the exterior wall 104*a* and 106*a* of instrument guide 100*a* of FIG. 7. That is, the cross-sectional configuration of the proximal end 303 of centering guide 300, as illustrated in FIG. 10, is configured to slide within space 200 of FIG. 7.

After performing a bilateral laminectomy, the cauda equina is retracted to one side and centering guide 300 is inserted along the midsagittal plane of the intervertebral space with edges 308 facing cranially and caudally to urge the vertebrae to the desired amount of distraction. In addition, and as discussed in U.S. Ser. No. 08/921,001, the distraction portion 305 can have a diverging or converging taper, relative to the longitudinal axis $X_1$—$X_1$ to create a desired degree of lordosis. The distal end 302 includes stops 312 of the illustrated embodiment to affirmatively stop distal advancement of centering guide 300 into the intervertebral space.

Once in position, the retraction of the cauda equina can be released and guide tube 100*a* can be slid over the proximal region 304 of centering guide 300 until the paddles abut the posterior aspect of the intervertebral space. Slits can be cut into the disc with a scalpel to mark the location where the paddles will be inserted into the disc space. After confirming that the cauda equina and nerve roots are clear, the instrument guide is tapped to urge the paddles into the intervertebral space until the shoulders at the distal end of the lateral guide affirmatively stop distal advancement.

From the foregoing detailed description and examples, it will be evident that modifications and variations can be made in the devices and methods of the invention without departing from the spirit or scope of the invention.

Therefore, it is intended that all modifications and verifications not departing from the spirit of the invention come within the scope of the claims and their equivalents.

We claim:

1. An instrument guide for implanting a spinal implant between opposing vertebral bodies, the instrument guide comprising:

a first member including a first proximal region having a tubular configuration and a first distal region having a first lateral guide surface, the first lateral guide surface having a first distal end;

a second member having a second proximal region including a tubular configuration and a second distal region having a second lateral guide surface, the second lateral guide surface having a second distal end;

the second member being fixed adjacent and parallel to the first member.

2. The instrument guide according to claim 1 wherein a cross sectional geometry of the first and second proximal regions are circular.

3. The instrument guide according to claim 1 having a first distal extension extending distally from the first distal end and a second distal extension extending distally from the second distal end.

4. The instrument guide according to claim 3 wherein the first lateral guide surface has a transverse cross-section dimension that is greater than a transverse cross-section dimension of the first distal extension and the second lateral guide surface has a transverse cross-section dimension that is greater than a transverse cross-section dimension of the second distal extension.

5. The instrument guide according to claim 3 wherein the first and second distal extensions each have a tapered distal tip.

6. The instrument guide according to claim 1 further comprising a removable first medial guide surface and a removable second medial guide surface.

7. The instrument guide according to claim 6 wherein the first medial guide surface and the second medial guide surface are each a tubular sleeve.

8. The instrument guide according to claim 6 wherein the first medial guide surface is a first radiused guide wall and the second medial guide surface is a second radiused guide wall.

9. The instrument guide according to claim 7 wherein a portion of the first medial guide surface and a portion of the second medial guide surface can each independently slide within the tubular configuration of the first proximal region and second proximal region, respectively.

10. The instrument guide according to claim 8 wherein the first medial guide surface and the second medial guide surface can each independently slide over a portion of an exterior surface of the tubular configuration of the first proximal region and the second proximal region, respectively.

11. The instrument guide according to claim 6 wherein the first medial guide surface has a first medial distal end and the second medial guide surface has a second medial distal end and each guide surface can independently slide distally such that the first medial distal end does not extend beyond the first distal end and the second medial distal end does not extend beyond the second distal end.

12. The instrument guide according to claim 7 wherein each of the tubular sleeves includes a proximal end, each proximal end including a handle for operating the tubular sleeve.

13. The instrument guide according to claim 8 wherein each of the first and second radiused guide walls include a proximal end, each proximal end including a handle for operatingly sliding the guide surfaces.

14. The instrument guide according to claim 1 wherein the first proximal region and second proximal region each include a stopping arrangement for selectively stopping distal advancement of an instrument passed through the instrument guide.

15. The instrument guide according to claim 14 wherein the stopping arrangement is a spacer cap.

16. A method for implanting a spinal implant between a first and second adjacent vertebrae of a patient through a posterior approach, the method comprising a step of:

positioning an instrument guide against a posterior aspect of the first and second adjacent vertebrae wherein the instrument guide comprises a first member having a tubular proximal region and a second member having a tubular proximal region and wherein the first member is fixed adjacent and parallel to the second member.

17. The method according to claim 16 wherein the first member includes a distal region having a first lateral guide surface and the second member includes a distal region having a second lateral guide surface.

18. The method according to claim 17 wherein the distal region of the first member includes a removable first medial guide surface and the distal region of the second member includes a removable second medial guide surface.

19. The method according to claim 18 wherein the first and second medial guide surfaces are radiused walls.

20. The method according to claim 18 wherein the first and second medial guide surfaces are tubular sleeves.

* * * * *